(12) United States Patent
Michelman et al.

(10) Patent No.: US 6,296,605 B1
(45) Date of Patent: Oct. 2, 2001

(54) HIGH-PRESSURE DRIVE SYSTEM

(75) Inventors: Paul C. Michelman, New York, NY (US); R. Mitchell Baldwin, II, Grand Rapids, MI (US); Howard R. Levin, Teaneck, NJ (US)

(73) Assignee: Paramount Capital Investments, LLC, New York, NY (US)

( * ) Notice: Subject to any disclaimer, the term of this patent is extended or adjusted under 35 U.S.C. 154(b) by 0 days.

(21) Appl. No.: 09/344,209

(22) Filed: Jun. 24, 1999

Related U.S. Application Data
(60) Provisional application No. 60/090,439, filed on Jun. 24, 1998.

(51) Int. Cl.[7] ........................................ A61M 1/10
(52) U.S. Cl. ........................................................ 600/16
(58) Field of Search .................................. 600/16, 17, 18

(56) References Cited

U.S. PATENT DOCUMENTS

| | | | |
|---|---|---|---|
| 3,465,746 | * 9/1969 | Guarino | 600/17 |
| 4,016,871 | 4/1977 | Schiff | 128/2.06 R |
| 4,648,385 | * 3/1987 | Oumi et al. | 128/1 |
| 5,059,167 | * 10/1991 | Lundquist et al. | 600/17 |

* cited by examiner

Primary Examiner—William E. Kamm
(74) Attorney, Agent, or Firm—Darby & Darby (57) ABSTRACT

A high pressure inflation system for driving an inflatable heart assistance device. The system includes a fluid source for supplying a fluid at a relatively high pressure and a compression tank plumbed in selective communication with the pneumatic source. The compression tank is operative to store a predetermined volume of the pressurized fluid at approximately the high pressure created by the fluid source. A transfer valve is disposed downstream of the compression tank and is coupled to the heart assistance device. The compression tank and transfer valve are maintained in close proximal relation to the heart assistance device with the transfer valve being responsive to predetermined signals to expose the heart assistance device to the compression tank pressure and expand the device to compress and assist the heart.

20 Claims, 6 Drawing Sheets

FIG. 9

HIGH-PRESSURE DRIVE SYSTEM

CROSS-REFERENCED TO RELATED APPLICATIONS

This application claims priority pursuant to 35 U.S.C. §119 based upon U.S. provisional application Ser. No. 60/090,439 filed Jun. 24, 1998, the entire disclosure of which is hereby incorporated by reference.

FIELD OF THE INVENTION

The invention relates to drive systems for mechanically assisting the heart and more particularly to a high-pressure inflation system capable of controlling an adjustable pressure pulse applied to a cardiac compression apparatus. The applied pressure pulse can be adjusted with a high degree of accuracy with regard to the plateau pressure.

BACKGROUND OF THE INVENTION

An important life-saving technique for individuals diagnosed with weakened hearts includes mechanically assisting the heart to pump blood. Assistance to the heart ensures an adequate blood pressure for sufficiently supplying blood throughout the body without undue stress on the heart muscle. Typically, a device such as a heart compression apparatus, or cuff, carries out the assistance during invasive surgery. An alternative related application for the apparatus involves cardiopulmonary resuscitation (CPR) techniques to rhythmically squeeze the heart in cases where the heart fails to beat at all.

Those skilled in the art have proposed a variety of devices to successfully carry out the heart compression function to maximize support for the heart and provide reliable and accurate functionality. One such cuff device, disclosed in pending Provisional U.S. patent application Ser. No. 60/028, 722, filed on Oct. 18, 1996 and assigned to the assignee of the present invention, carries and supports the heart during invasive surgery while uniformly applying pressure directly to the heart through means of an inflatable liner. The liner is cyclically inflated and deflated by an inflation system to apply pressure to the heart.

Because each heart pumps blood according to a pressure profile unique for each patient, successful cardiac compression on the inflatable liner depends upon the inflation system being controllable to somewhat match the patient's personal cardiac rhythm or pressure profile. An equally important consideration involves the limited duration of the heart's systolic cycle, which provides only about fifty to one-hundred milliseconds within which to establish synchronous compression.

One proposal for pneumatically driving a cardiac compression device, such as an Anstadt cup or intra-aortic balloon, is disclosed in U.S. Pat. No. 4,016,871. The pneumatic drive system is housed within a console and includes a relatively low-pressure compressor coupled in parallel to a pressure regulator and a vacuum regulator. The respective regulators are connected to respective reservoirs having outputs coupled to respective solenoid valves. The solenoid valves are controlled by an electronic sequencer to pass pressurized pulses through an elongated pressure line coupling the console to the cardiac compression device for inflation and deflation thereof.

A second proposal, such as that disclosed in U.S. Pat. No. 5,300,017, describes a driver for a cardiac compression device including an isolator with respective first and second chambers separated by a flexible diaphragm. The first chamber is coupled through respective positive and negative pressure switching valves to respective positive and negative air pressure sources. The second chamber of the isolator communicates directly with the cardiac compression device. The diaphragm responds to positive or negative pressures in the range of about 10 mmHg from the respective sources to decrease or increase the volume within the second chamber, thereby pressurizing or depressurizing the cardiac compression device.

While these proposals appear to work well for their intended applications, they are often disposed several feet from the cardiac compression device. This is typically because of the controlled conditions associated with surgical environments. As a result, the extended length of the pressure line generally requires a relatively large diameter tube to minimize line resistance. The increase in volume, as a consequence, increases the overall flowrate through the system, thereby increasing the component sizes and costs.

What is needed and heretofore previously unavailable is a high-pressure drive system for a cardiac compression device, such as a cuff, that enables reduced component sizes and improved rise-time response. A further need exists for such a system having improved safety features for patient protection. The high-pressure drive system of the present invention satisfies these needs.

SUMMARY OF THE INVENTION

The system of the present invention provides the capability of miniaturizing the components necessary to effect pressure pulses to inflate a heart assistance device. The system also serves to improve inflation performance by reducing rise times for the respective pressure pulses, and maintaining a high level of safety for patients.

To realize the above advantages, in one form the invention comprises a high-pressure inflation system for driving an inflatable heart assistance device. The system includes a fluid source for supplying a fluid at a relatively high pressure and a compression tank plumbed in selective communication with the pneumatic source. The compression tank is operative to store a predetermined volume of the pressurized fluid at approximately the high pressure created by the fluid source. A transfer valve is disposed downstream of the compression tank and is coupled to the heart assistance device. The compression tank and transfer valve are maintained in close proximal relation to the heart assistance device with the transfer valve being responsive to predetermined signals to release the pressurized fluid from the compression tank to fill the heart assistance device and expand the device to compress and assist the heart.

In another form, the invention comprises a transfer valve for switching a load between respective pressurizing and venting states in response to signals generated by a controller. The transfer valve includes respective pressure and venting ports and an output port directly coupled to the load. The output port is alternately coupled to the pressure and venting ports through a spring-biased switching mechanism.

In one embodiment, the invention includes a convenient safety mechanism. The safety mechanism guarantees that the inflated cuff vents to atmosphere in the event of a failure in the drive system. This is accomplished by monitoring the cuff pressure and opening the safety valve when the pressure remains high.

Other features and advantages of the present invention will be apparent from the following detailed description when read in conjunction with the accompanying drawings.

DETAILED DESCRIPTION OF THE INVENTION

The high-pressure drive system of the present invention provides improved response characteristics for pressure pulse rise-times during inflation of a cardiac compression device, or cuff. The performance improvement results from the implementation of miniaturized pressure components disposed proximate to the assistance device to minimize resistance through a relatively short pressure line and maximize system response.

Figures 1, 3:
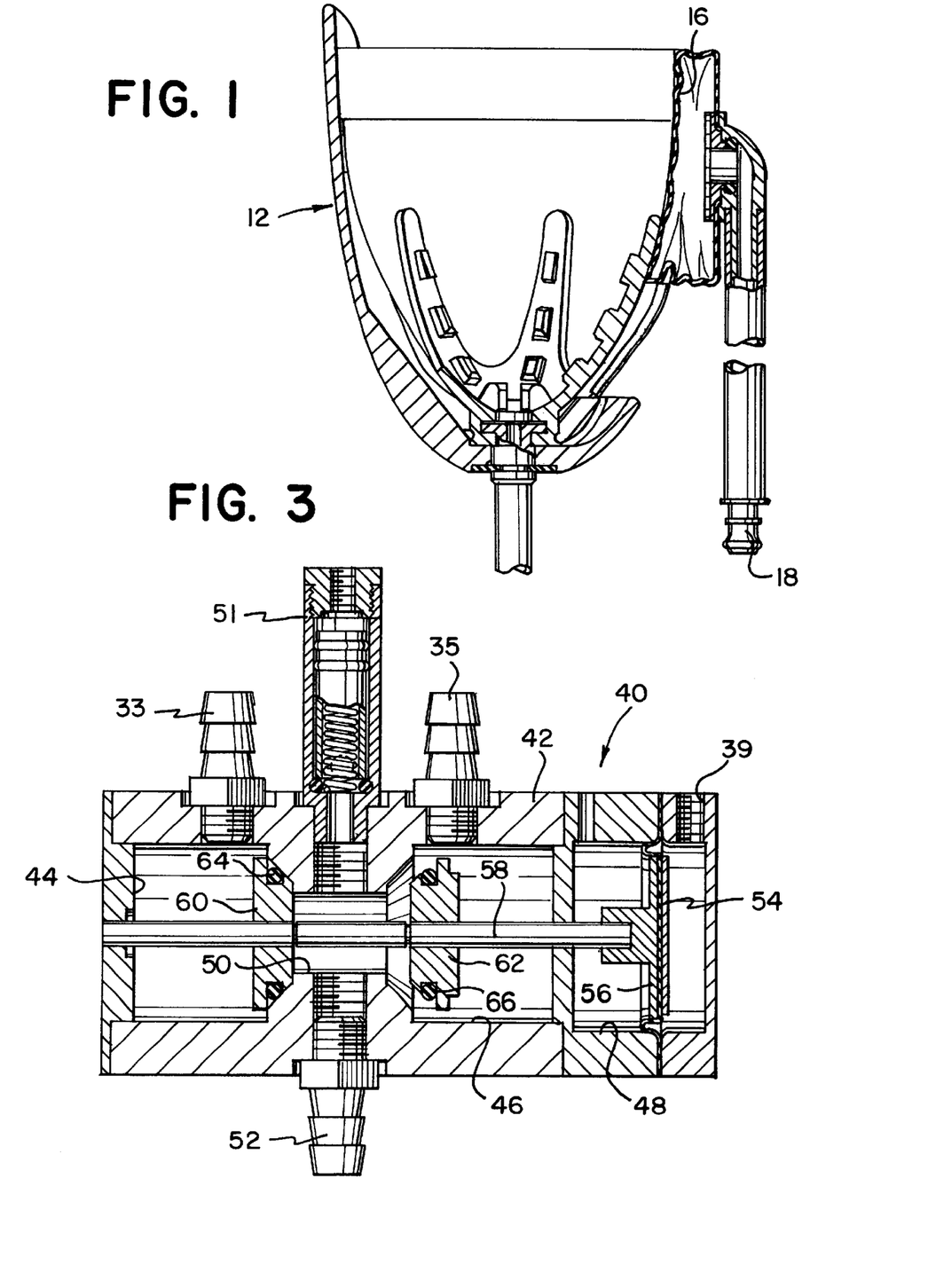
FIG. 1 is a cross-sectional view of a cardiac assistance cuff aiding a heart to illustrate an important application for the inflation system of the present invention.
FIG. 3 is a longitudinal cross-sectional view of a transfer valve employed in the system of FIG. 2.

By way of example, FIG. 1 illustrates a cardiac compression apparatus or cuff 12 for assisting a heart (not shown) to pump blood through a vasculature by compressing the heart ventricle during the systolic phase. An example of such an apparatus is disclosed in pending U.S. Provisional Patent Application Ser. No. 60/064086, filed Nov. 3, 1997, and titled "A Ventricular Cuff For Assisting a Heart to Pump Blood By Applying Substantially Uniform Pressure to at Least a Portion of the Ventricles," the disclosure of which is expressly incorporated by reference. The heart is placed into the apparatus which is lined with an internal inflation chamber or liner 16 that includes a port 18 for connecting to a high-pressure drive system according to the present invention.

Figure 2:
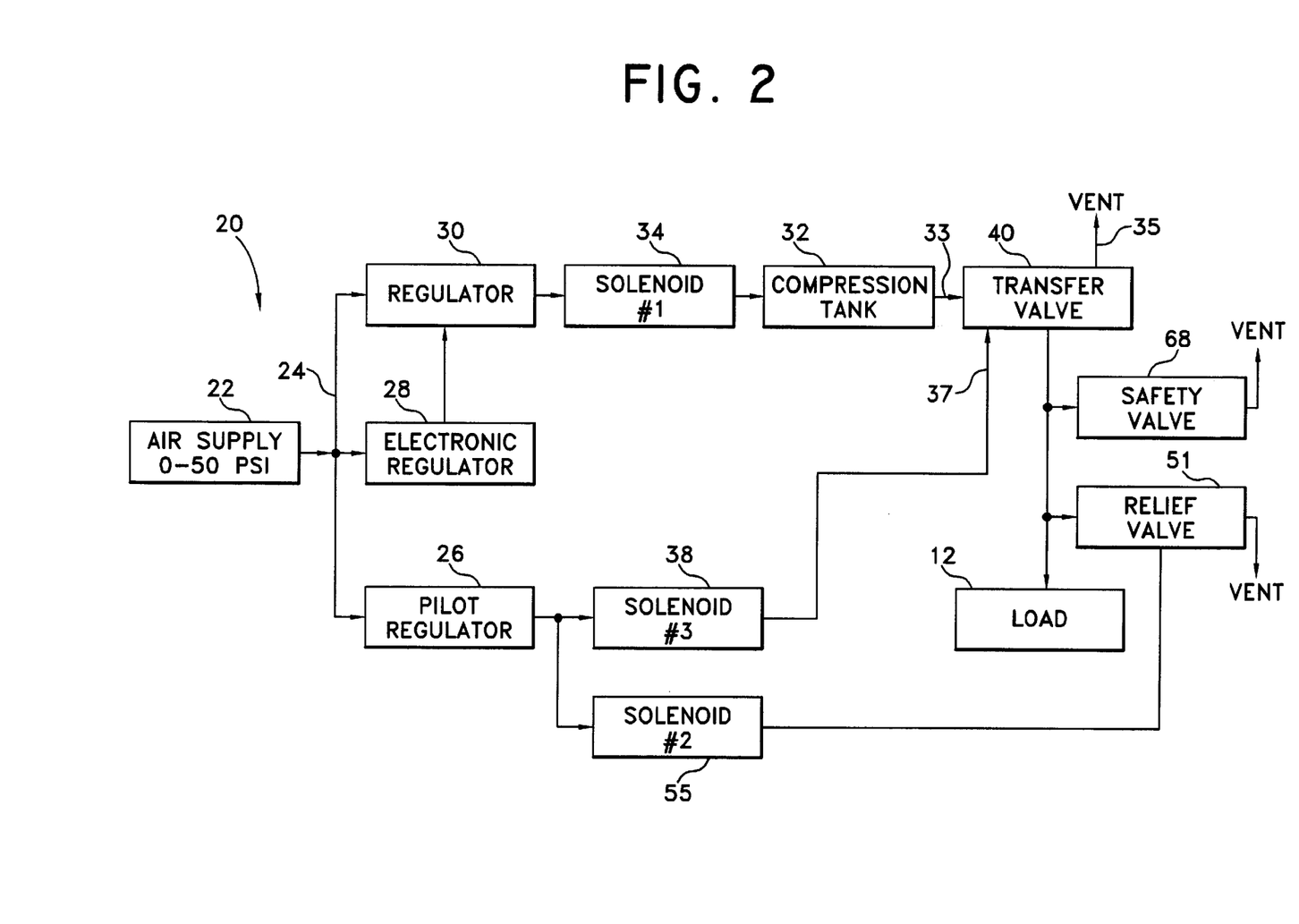
FIG. 2 is a block diagram of a high-pressure drive system according to one embodiment of the present invention.

Referring now to FIG. 2, a high-pressure drive system according to one embodiment, generally designated 20, includes a high-pressure pneumatic supply source or compressor 22 capable of providing pressurized gas at pressures in the range of approximately 0 to 50 psi. The supply source couples to a pressure manifold 24 which distributes the pressurized gas to a pilot regulator 26, an electronic regulator 28, and a primary regulator 30. The electronic regulator maintains an output air pressure substantially proportional to applied voltage and provides a controllable reference pressure for the primary regulator.

A compression tank 32 is disposed downstream of the primary regulator 30 and selectively communicates with the regulator through a first solenoid valve 34, and a transfer valve 40. The compression tank is formed from an elongated section of tubing of about one meter length with a tube diameter of approximately one-half inch. The tank includes an inner chamber having a volume of compressed gas on the order of approximately 100 to 500 ml.

Referring again to FIG. 2, and more particularly to FIG. 3, the transfer valve 40 includes a cylindrical hollow housing 42 formed with respective pressure, vent and control chambers 44, 46 and 48. The respective chambers have respective openings or ports 33, 35, and 39. The pressure and vent chambers are alternatively coupled through a passage 50 to an outlet port 52. The passage is selectively opened to the vent or pressure chamber. A biased actuator 54, initially biased in a normally closed state (vent), alternatively couples either the vent chamber 46 or the pressure chamber 44 to the outlet 52 that is, in turn, connected to the cuff 12. The actuator comprises a piston 56 mounted to the distal end of a biased, and axially slidable shaft 58. A pair of spaced-apart poppets 60 and 62 having respective O-ring seals 64 and 66 are mounted intermediate the shaft to alternatively seal the passage 50 from the vent chamber 46 (simultaneously opening the path to the pressure chamber 44) in response to a control pressure placed on the piston in the control chamber 48. The bias placed on the shaft ensures that the actuator automatically vents when no power is applied to the transfer valve, or when power is lost to the valve.

The high-pressure drive system of the present invention also includes several safety features that minimize concerns regarding the placement of relatively high pressure lines proximate a patient. For example, to effect reliable operation of the actuator 54, one embodiment of the valve employs a close-fitting ceramic surface spool valve (not shown) to perform the actual switching. The spool valve requires no lubrication, exhibits excellent wear characteristics, and is resistant to fouling from fluid contamination. A pressure relief valve 51 is mounted to the transfer valve 40 and is disposed opposite the outlet port 52 and is coupled to the passage 50 to rapidly exhaust gas when a factory set pressure limit is exceeded, typically between 200–250 mmHg. The relief valve is also responsive to activation of a second solenoid valve 55 to relieve pressure in the cuff. Further, the transfer valve includes a fail safe neutral position that returns the valve to its exhaust state if power is lost. Additionally, redundancy is built into the vent portion of the system through implementation of an electronically controlled safety valve 68 (FIG. 2) that detects and corrects any failure of the transfer valve venting capability. The safety valve provides a secondary vent path that releases the gas from the cuff 12 when the system detects that the pressure in the cuff has not returned to atmosphere for approximately one second.

The compression tank 32 and transfer valve 40 can be conveniently supported on an IV pole or other mount (not shown) which allows for proximal placement of the components near the cardiac compression device on the order of approximately one meter or less.

Figure 4:
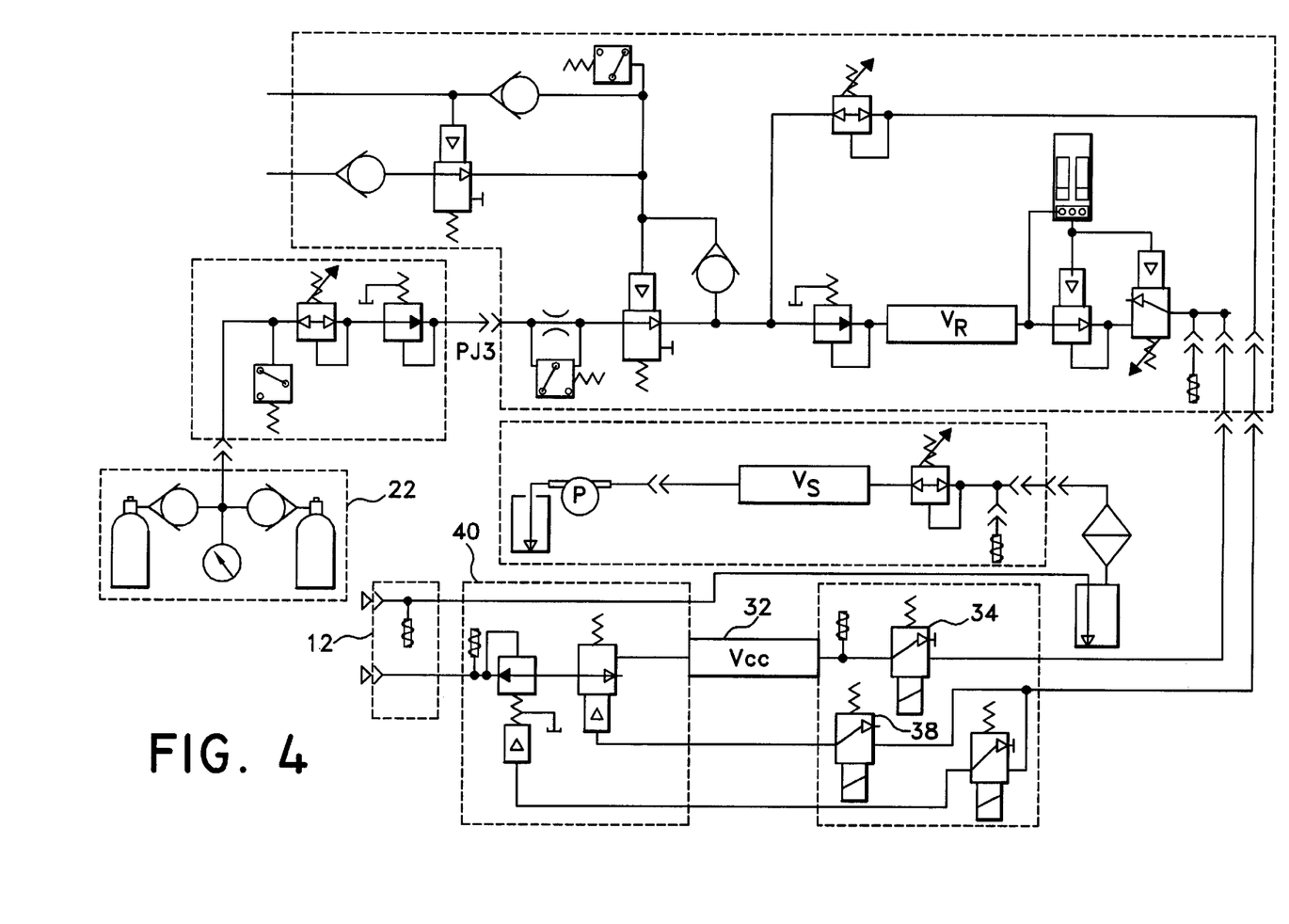
FIG. 4 is a detailed pneumatic schematic of the drive system of FIG. 2.

To generate the pneumatic sequencing signals for the respective solenoids, the system 20 employs a dedicated microprocessor (not shown) responsive to programmed commands. The microcomputer and programmed software control the overall rate, the cuff inflation duration, compression tank control pressure, and inflation delay for synchronous operation. A detailed schematic of the system 20 is shown in FIG. 4. Preferably, the high-pressure system components are distributed between a control console (not shown) and a tether (not shown). The compression tank 32, transfer valve 40 and control solenoid valves 34 and 55 are disposed in the tether, while the pressure regulators 26 and 28 are set in the control console. Pressure sensors (not shown) for monitoring and safety are also located in the tether.

Figure 5:
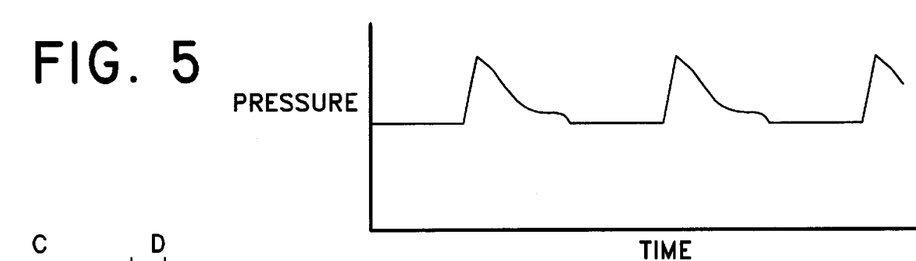
FIG. 5 is a graphical view of a typical load pressure waveform produced by the system of FIG. 1.

In operation, the high-pressure drive system 20 produces sequenced pressure pulses, similar to those shown in FIG. 5, to inflate and deflate the cardiac compression device according to a pre-programmed profile. Referring to the sequencing scheme illustrated in FIGS. 6 and 7, prior to T0 (state A), the first solenoid valve 34 energizes to pressurize the compression tank 32 with regulated pressurized gas from the pneumatic source 22.

Figures 6, 7:
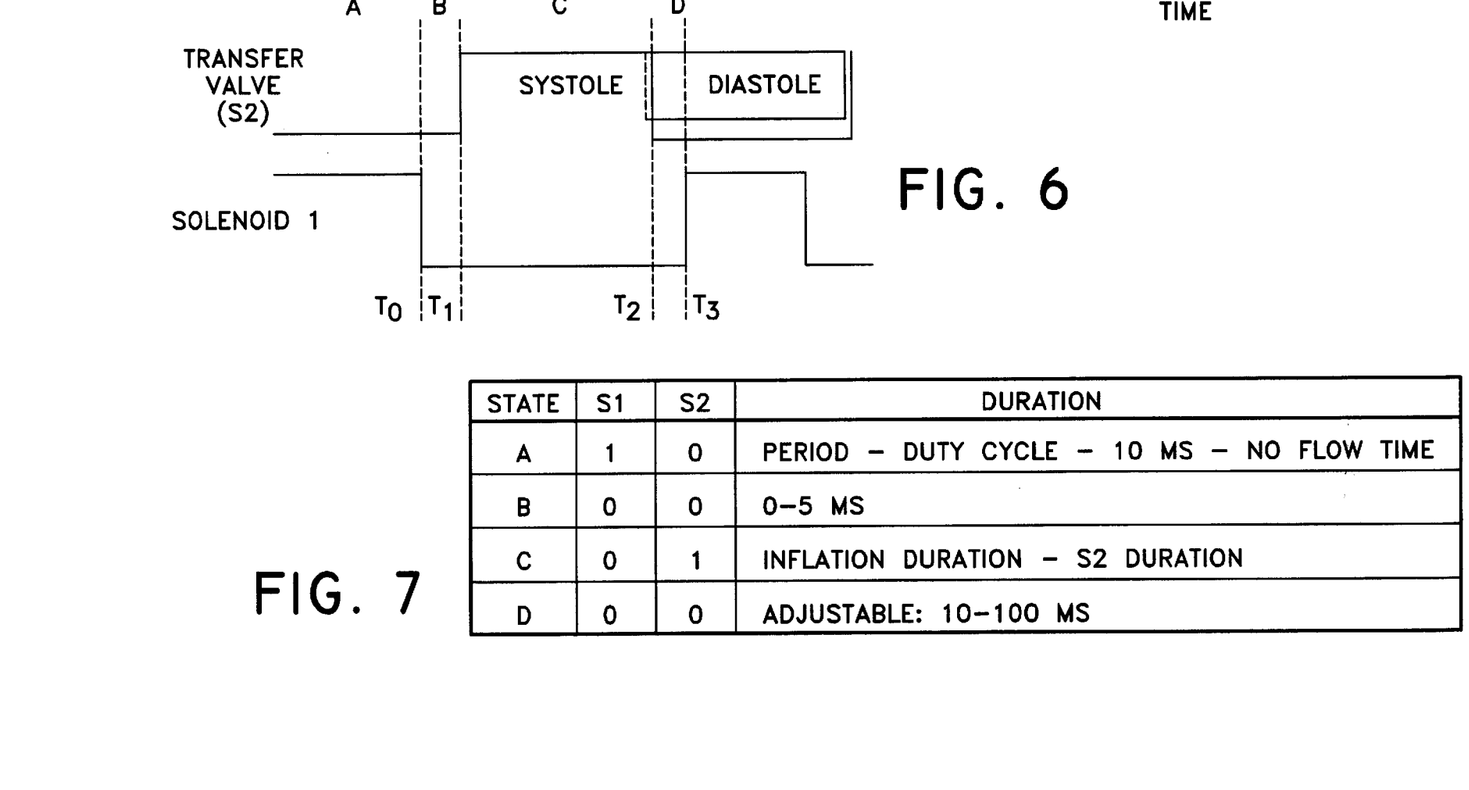
FIG. 6 is a timing diagram for sequencing valves employed in the system of FIG. 1.
FIG. 7 is a state diagram for the valve sequencing of FIG. 6.

While the compression tank pressurizes, the transfer valve 40, isolated from the compression tank due to the inactivation of the third solenoid valve, vents the cuff to atmosphere through the continued deactivation of the third solenoid valve 38. Once the compression tank pressurizes, at T0, the solenoid valve 34 de-energizes to signal a no-flow period of approximately zero to ten milliseconds (state B). The no flow period ensures no direct connection between the pneumatic source and the cardiac compression device.

Following the no-flow period, the third solenoid 38 energizes at T1 to drive the transfer valve 40 from its venting state to its flow-through state (state C). As the transfer valve actuates, the load pressure increases suddenly to inflate the cuff 12 with a pressure pulse having a steep rise time on the order of approximately 15–20 milliseconds. As the load decreases in volume during a contraction of the heart, the pressure in the cuff decreases until it reaches equilibrium. During the latter stages of the systolic portion of the cycle, the pressure between the first solenoid 34 and the cuff maintains an equilibrium at the "plateau pressure".

Further referring to FIG. 6, at time T2, the third solenoid 38 de-energizes to switch the transfer valve from a "flow-through" state to a vent state for deflating the cuff 12. During this time, the first solenoid 34 remains deactivated for a measurable period of time (state D) to ensure that no direct connection exists between the pneumatic source 22 and the cuff. Should the transfer valve fail to vent properly, either the relief valve 51 or the safety valve 68 will relieve and redirect the pressurized gas from the cuff to place the cuff in a depressurized state. This happens either from the safety valve detecting an over pressurized condition for more than one second during the expected vent state, or from a command supplied by the second solenoid 55 to open the relief valve 51 and vent the cuff pressure. The relief valve also serves to vent the cuff pressure at any time that unacceptably high pressures are detected in the cuff.

At the conclusion of the second no-flow period, the first solenoid valve 34 is re-energized to repeat the inflation and deflation cycle.

It should be understood that the inflation/deflation cycle is triggered from one of two sources, depending on whether the system is operating in assist mode or CPR mode. In assist mode, inflation (state C) begins in synchrony with the native heart contraction. In CPR mode, the entire cycle operates at a fixed rate as controlled by the operator.

Figure 8:
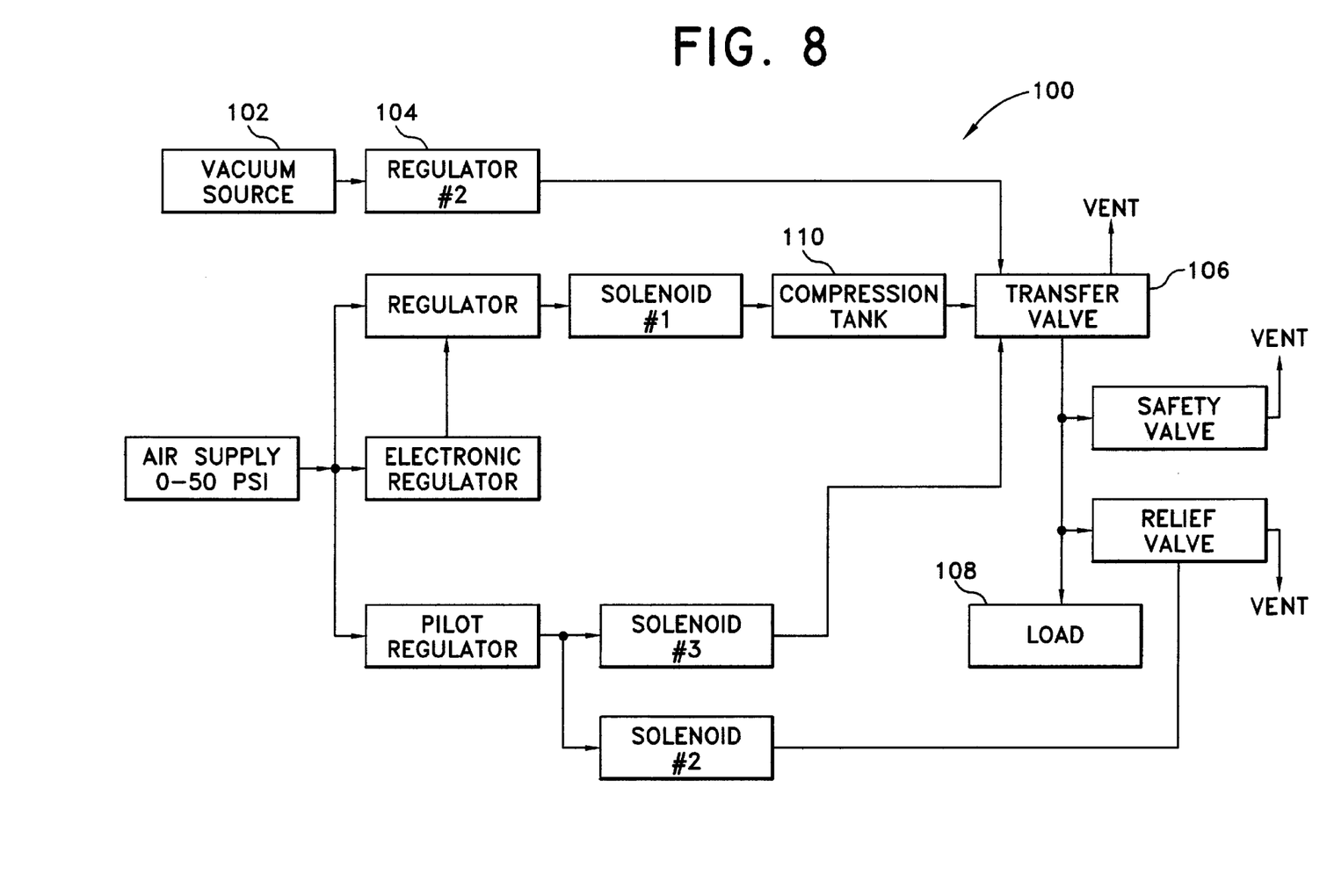
FIG. 8 is a block diagram of a high-pressure drive system according to a second embodiment of the present invention.

Referring now to FIG. 8, the high-pressure drive system according to a second embodiment, generally designated 100, is substantially similar to the first embodiment and includes a vacuum source 102 in the range of 0–200 mmHg and coupled through a vacuum regulator 104 to a transfer valve 106 to quickly deflate a load 108, such as a cardiac compression device or cuff.

Deflation takes place through a vacuum tank (not shown) which is preferably disposed concentrically around a compression tank 110. This construction allows the placement of the vacuum tank as close to the compression device as possible to enable quick deflation.

In operation, the compression device is exposed to the vacuum during the stage of operation where the transfer valve switches from "flow-through" mode to vent mode. Overall, sequencing of the second embodiment is substantially similar to that of the first embodiment.

Figure 9:
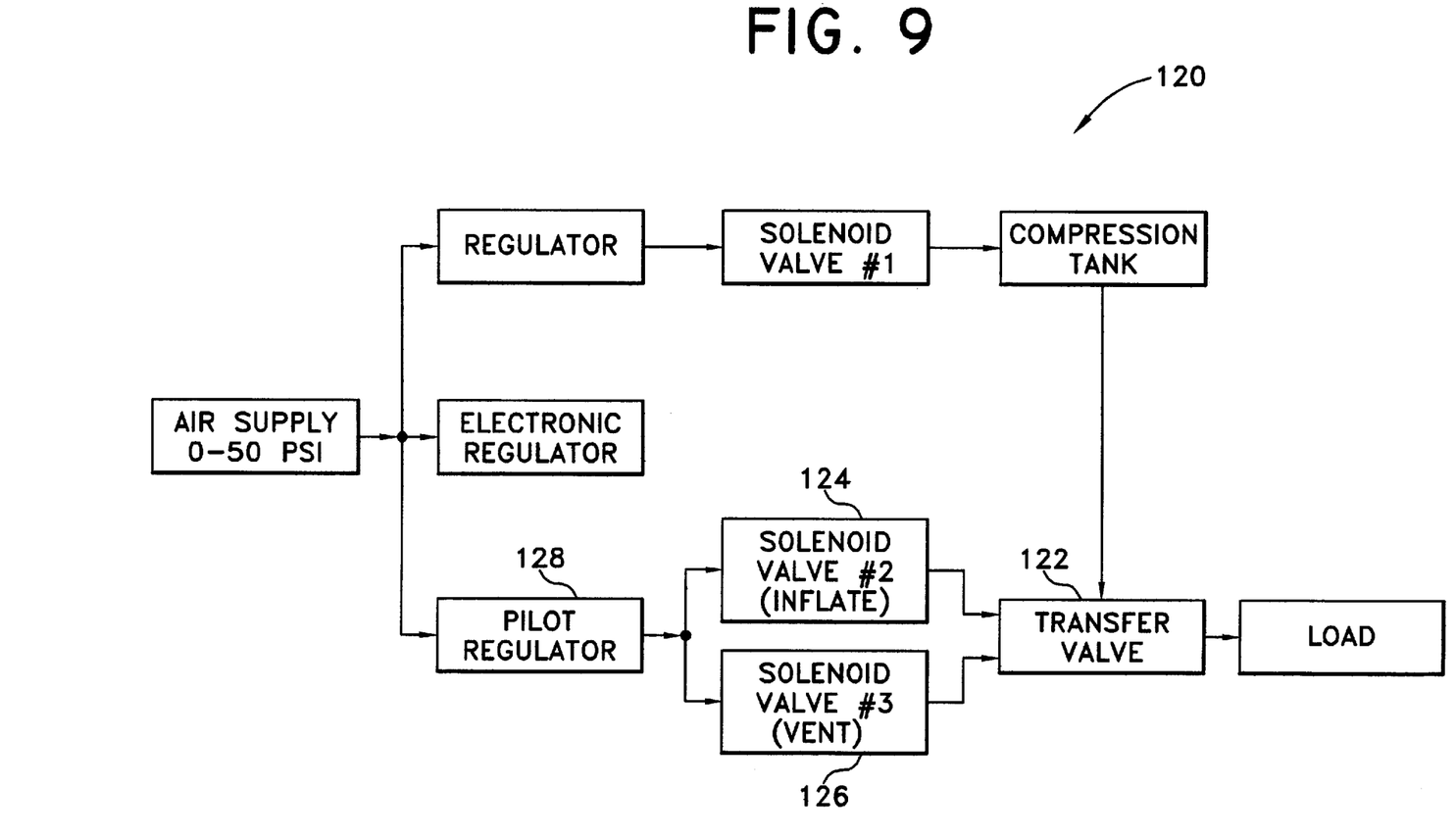
FIG. 9 is a block diagram of a high-pressure drive system according to a third embodiment of the present invention.

A further embodiment, generally designated 120, is shown in FIG. 9, which includes many of the features of the first embodiment 20. One primary difference, however, is in the construction involving the transfer valve 122, which couples directly to a second solenoid valve 124 for inflation, and a third solenoid valve 126 for deflation. In this manner, the transfer valve is driven into its respective inflation and deflation states by air pressure supplied through the pilot regulator 128.

Those skilled in the art will appreciate the many benefits and advantages offered by the present invention. Of significant importance is the use of a high-pressure source to charge a compression tank maintained in proximal relation to a cardiac compression device. This allows a substantial reduction in the size of the pressure components in the system with corresponding reductions in component cost. Moreover, the use of high pressure disposed in proximal relation to drive the cardiac compression device provides significant performance improvements in the form of faster rise times for generated pressure pulses.

A further important advantage offered by the present invention is the utilization of a unique transfer valve employing safety features that protect patients from relatively high pressures in the respective pneumatic lines.

While the invention has been particularly shown and described with reference to the preferred embodiments thereof, it will be understood by those skilled in the art that various changes in form and detail may be made therein without departing from the spirit and scope of the invention.

What is claimed is:

1. A high pressure inflation system for driving an inflatable heart assistance device, said system including:
    a fluid source for supplying a fluid at a relatively high pressure;
    a compression tank plumbed in selective communication with said pneumatic source and operative to store a predetermined volume of said pressurized fluid at approximately said high pressure;
    a controller for generating predetermined sequencing signals for inflation and deflation of said heart assistance device; and
    a transfer valve disposed downstream of said compression tank and coupled to said heart assistance device, said compression tank and transfer valve maintained in close proximal relation to said heart assistance device, said transfer valve responsive to said predetermined sequencing signals to couple said heart assistance device to said compression tank and expand said device with said pressurized fluid to compress and assist said heart, said transfer valve further including a vent port responsive to predetermined vent signals to connect said expanded device to said vent port to deflate said compression device.

2. A high pressure inflation system according to claim 1 and further including:
    a vacuum source coupled to said transfer valve vent port to deflate said compression device at a relatively high rate.

3. A high pressure inflation system according to claim 2 wherein:
    said fluid source supplies fluid at a pressure within the range of 0–50 PSI.

4. A high pressure inflation system according to claim 1 wherein:
    said compression tank comprises an elongated section of tubing defining an internal chamber for storing a predetermined volume of compressed gas.

5. A high pressure inflation system according to claim 5 wherein:
said internal chamber is sized to store a volume of gas within the range of approximately 100 to 500 milliliters.

6. A high pressure inflation system according to claim 1 wherein:
said transfer valve includes respective pressure and venting ports and an output port directly coupled to said cardiac compression device, said output port being alternately coupled to said pressure and venting ports through a switching mechanism.

7. A high pressure inflation system according to claim 7 wherein:
said switching mechanism comprises a spring-biased piston disposed within a piston chamber.

8. A high pressure inflation system according to claim 6 wherein:
said switching mechanism includes a shaft-driven actuator to effect switching between said inflation and deflation states.

9. A high pressure inflation system according to claim 10 wherein said actuator comprises:
a shaft;
a piston mounted to the distal end of said shaft; and
a pair of spaced-apart poppets having respective O-ring seals.

10. A high pressure inflation system according to claim 1 and further including:
an IV pole unit; and
said compression tank and said transfer valve are supported on said IV pole unit.

11. A high pressure inflation system according to claim 10 wherein:
said compression tank and said transfer valve are disposed within one meter of said compression device.

12. A high pressure inflation system according to claim 1 wherein:
said transfer valve includes a pressure relief mechanism.

13. A high pressure inflation system according to claim 1 wherein:
said transfer valve includes a fail-safe neutral position to return the valve to a venting mode if power to the valve is lost.

14. A high pressure inflation system according to claim 1 wherein:
said controller comprises an electronic regulator.

15. A high pressure inflation system according to claim 1 wherein:
said switching mechanism comprises a spring-biased piston disposed within a piston chamber.

16. A high pressure inflation system according to claim 1 wherein:
said switching mechanism includes a shaft-driven actuator to effect switching between said inflation and deflation states.

17. A high pressure inflation system according to claim 16 wherein said actuator comprises:
a shaft;
a piston mounted to the distal end of said shaft; and
a pair of spaced-apart poppets having respective O-ring seals.

18. A high pressure inflation system according to claim 1 wherein:
said transfer valve includes a pressure relief mechanism.

19. A high pressure inflation system according to claim 1 wherein:
said transfer valve includes a fail-safe neutral position to return the valve to a venting mode if power to the valve is lost.

20. A high pressure inflation system according to claim 1 wherein:
said transfer valve includes a close-fitting ceramic surface spool valve to effect switching between said inflation and deflation states.

* * * * *